United States Patent
Lanciault et al.

(10) Patent No.: US 9,056,265 B2
(45) Date of Patent: *Jun. 16, 2015

(54) ISOLATED BIOACTIVE COMPOUNDS AND METHOD OF USE

(75) Inventors: David P. Lanciault, Plano, TX (US); Robert N. Ames, Pilot Point, TX (US)

(73) Assignee: Tenfold Technologies, LLC, Pilot Point, TX (US)

( * ) Notice: Subject to any disclaimer, the term of this patent is extended or adjusted under 35 U.S.C. 154(b) by 434 days.

This patent is subject to a terminal disclaimer.

(21) Appl. No.: 13/489,023

(22) Filed: Jun. 5, 2012

(65) Prior Publication Data

US 2012/0297846 A1 Nov. 29, 2012

Related U.S. Application Data

(63) Continuation-in-part of application No. 12/455,718, filed on Jun. 5, 2009, now Pat. No. 8,262,912.

(51) Int. Cl.

| | |
|---|---|
| *B01D 15/34* | (2006.01) |
| *B01D 21/26* | (2006.01) |
| *B01D 21/01* | (2006.01) |
| *B01D 17/00* | (2006.01) |
| *C02F 1/52* | (2006.01) |
| *C02F 9/00* | (2006.01) |
| *C02F 11/12* | (2006.01) |

(Continued)

(52) U.S. Cl.
CPC ............ *B01D 15/34* (2013.01); *B01D 17/00* (2013.01); *B01D 21/01* (2013.01); *C02F 11/12* (2013.01); *B01D 11/0288* (2013.01); *C05F 11/10* (2013.01); *C02F 9/00* (2013.01); *C05F 11/06* (2013.01); *C02F 1/5236* (2013.01); *C02F 1/5245* (2013.01); *B01D 21/26* (2013.01); *B01D 11/02* (2013.01); *A01N 63/02* (2013.01)

(58) Field of Classification Search
CPC ........ B01D 15/34; B01D 15/38; B01D 21/00; B01D 21/01; A01N 63/02; C05F 11/00; C05F 11/08; C05F 11/10
USPC ......... 210/632, 635, 638, 639, 656, 702, 737, 210/738, 770, 774, 787, 804, 806; 71/1, 71/8–11, 23; 435/41, 243; 424/115, 123, 424/124; 47/58.1 R, 58.1 C, 58.1, 48.5, 47/58.1 SC; 504/116.1, 117, 118
See application file for complete search history.

(56) References Cited

U.S. PATENT DOCUMENTS

| | | |
|---|---|---|
| 2,556,376 A | 6/1951 | Regna et al. |
| 2,756,134 A | 7/1956 | Novak |

(Continued)

FOREIGN PATENT DOCUMENTS

| | | |
|---|---|---|
| EP | 287152 | 4/2008 |
| WO | 9113835 | 9/1991 |

(Continued)

*Primary Examiner* — Joseph Drodge
(74) *Attorney, Agent, or Firm* — Schultz & Associates, P.C.

(57) ABSTRACT

Bioactive compounds extracted from a fermentation broth created by a unique microbial community during a fermentation process and fractionated into several fractions based on size. Four of the resulting fractions stimulate growth of plants that are planted in soil to which the fractions have been applied. The fractions can be applied to the soil individually or combined together prior to application. In another embodiment, the unique fractions can be freeze dried or spray dried.

87 Claims, 3 Drawing Sheets

(51) Int. Cl.
*C05F 11/06* (2006.01)
*C05F 11/10* (2006.01)
*A01N 63/02* (2006.01)
*B01D 11/02* (2006.01)

(56) References Cited

U.S. PATENT DOCUMENTS

| | | | |
|---|---|---|---|
| 2,901,864 A | 9/1959 | Hiler | |
| 4,018,593 A | 4/1977 | Muller | |
| 4,395,351 A | 7/1983 | Camp | |
| 4,666,497 A * | 5/1987 | Tenzer | 71/6 |
| 5,071,559 A | 12/1991 | Bleeker | |
| 5,387,271 A | 2/1995 | Crawford et al. | |
| 5,797,976 A * | 8/1998 | Yamashita | 71/26 |
| 6,309,440 B1 * | 10/2001 | Yamashita | 71/27 |
| 6,318,023 B1 | 11/2001 | Yamashita | |
| 6,336,772 B1 | 1/2002 | Yamashita | |
| 6,521,129 B1 | 2/2003 | Stamper et al. | |
| 6,682,578 B2 * | 1/2004 | Sower | 71/11 |
| 6,761,886 B2 | 7/2004 | Cheung | |
| 6,828,131 B2 | 12/2004 | Zhang | |
| 6,927,320 B1 | 8/2005 | Benfey et al. | |
| 6,979,444 B2 | 12/2005 | Cheung | |
| 6,994,850 B2 | 2/2006 | Cheung | |
| 7,014,768 B2 | 3/2006 | Li et al. | |
| 7,044,994 B2 | 5/2006 | Porubcan | |
| 7,255,890 B2 * | 8/2007 | Sanz Gutierrez | 426/656 |
| 8,002,870 B2 | 8/2011 | Yamashita | |
| 8,262,912 B1 * | 9/2012 | Lanciault et al. | 210/656 |
| 2003/0087454 A1 | 5/2003 | Schultz et al. | |
| 2004/0154988 A1 | 8/2004 | Sheets, Sr. | |
| 2006/0027496 A1 | 2/2006 | Campion et al. | |
| 2006/0130546 A1 | 6/2006 | Beaton et al. | |
| 2006/0194299 A1 | 8/2006 | Brinch-Pedersen et al. | |
| 2007/0191228 A1 | 8/2007 | Li et al. | |
| 2008/0009414 A1 * | 1/2008 | Ho et al. | 504/100 |
| 2010/0135978 A1 | 6/2010 | Svendsen et al. | |
| 2010/0135987 A1 | 6/2010 | Hickman et al. | |
| 2010/0310548 A1 | 12/2010 | Yeh et al. | |

FOREIGN PATENT DOCUMENTS

| | | |
|---|---|---|
| WO | 0039052 | 7/2000 |
| WO | 0044688 | 8/2000 |
| WO | 02070436 | 9/2002 |

* cited by examiner

Figure 1

P2          Control

Figure 2

P4 Control

Figure 3

ISOLATED BIOACTIVE COMPOUNDS AND METHOD OF USE

CROSS REFERENCE TO RELATED APPLICATION

This application is a continuation in part of U.S. application Ser. No. 12/455,718 filed on Jun. 5, 2009 now U.S. Pat. No. 8,262,912.

FIELD OF THE INVENTION

The present invention relates to the unique grouping of biological materials containing bioactive compounds and the isolation method thereof from a unique larger microbial community for improving plant growth. Methods of applying the unique grouping of bioactive compounds are also provided.

BACKGROUND OF THE INVENTION

Increasing plant growth and food production is a major concern around the world. As world populations increase, the need for more food production increases as well. However, the available land to produce food is decreasing due to soil degradation, salinity, reduced water quality, increased industrialization, and other land demands.

In addition to decreasing land for agriculture, there is also a demand for the protection of water supplies. Fertilizers and pesticides applied to the soil to increase food production can be washed away and enter surface and groundwater supplies. Nutrient loading of waterways is not healthy for humans or animals, and must be removed before the water is safe to drink or use.

Costs of fertilizers have increased due to energy and transportation costs, thus farm profits are negatively impacted. Farmers must find ways of maximizing the efficiency of fertilizers.

Water quality is decreasing in major agricultural regions of the United States and the world which further impacts the production of agricultural crops.

There are many ways known to increase plant growth, including application of nutrients (fertilizers and plant growth stimulants). The effects of these types of applications, however, are limited by the manner in which the plants and soil absorb and process these nutrients. Further, excess nutrients are usually applied to offset the amount of fertilizers that are leached away by rain and irrigation or that are immobilized or fixed in the soil and thus become unavailable for plant uptake.

It is also known in the industry that certain bacteria and microorganisms assist in plant growth. For example, bacteria are needed to fix atmospheric nitrogen and then convert this nitrogen to a plant-available form. Microorganisms are known to stimulate plant growth through solubilization of phosphorus or mineralization of other nutrients which then become available for plant uptake and growth. For these types of microorganisms to be used in commercial products, they must be maintained in pure, individual culture and mass produced when needed for assembly, possibly with other microorganisms or additives, into a final product. Since microorganisms are living cells, certain storage conditions must be maintained to keep the cells in a viable form.

Also known to science is the fact that interactions of microorganisms with their environment produces bioactive compounds, generally believed to be compounds such as proteins, small peptides, or other types of molecular structures, which can assist the microorganism in improving physical and chemical aspects of the soil, and stimulate plant growth and nutrient uptake in the plant. However, the exact nature and identification of the specific bioactive compounds that create these beneficial effects is still unknown.

Microorganisms and their bioactive compounds when applied to the soil, can stimulate plant root growth thereby increasing nutrient uptake. This improves the utilization of applied fertilizers thus reducing fertilizer loss and environmental impact.

One example of the use of microorganisms is disclosed in U.S. Patent Application No. 2006/0027496 by Campion, et al. In Campion, a lagoon system is described with anaerobic, facultative, and aerobic stratum whereby the aerobic stratum may be artificially induced by aeration, and additional aerobic bacteria may be artificially added. The system is designed to treat a manure slurry, and the liquid thereof, extracted from the aerobic stratum, may be applied to land as a fertilizer without further processing. Campion mentions the presence of "byproducts" and "growth stimulators" in the lagoon system design, but only in the context that these compounds provide nutrients or otherwise support bacterial fermentation and methanogenesis. Thus the bioactive compounds described by Campion function internally within the lagoon system to process a raw manure slurry. The biological content of the lagoon liquid is not disclosed.

An example of the use of a microbial community to produce a material to stimulate plant growth are products sold by Advanced Microbial Solutions, LLC ("AMS") of Pilot Point, Tex. under the trademarks and trade names SuperBio SoilBuilder®, SuperBio Ag Blend®, SuperBio SoilLife™, and NutriLife®. These products are sold by AMS and its licensees across the United States and overseas. These products are created from a unique community of microbes and biological material after a fermentation process. The AMS fermentation system results in the production of a fermentation extract solution containing live microorganisms and bioactive compounds. The base fermentation extract solution is sold as SuperBio SoilBuilder®, and serves as the primary ingredient for additional commercial products identified above. The fermentation extract solution contains many different species of microorganisms and many different bioactive compounds. However, it is unknown which specific types of bioactive compounds or the interaction between them produce the beneficial effects shown by the use of the fermentation extract solution of the prior art.

SUMMARY OF THE INVENTION

The solution disclosed by Applicants begins as a liquid fermentation extract solution containing both microorganisms and bioactive compounds. The fermentation extract solution is the liquid sold as SuperBio SoilBuilder®. The invention is the use of a known protein extraction method which leads to the concentration of bioactive compounds which are not identified as proteins with standard protein identification techniques.

The original fermentation extract solution is clarified by centrifugation or filtration to remove suspended materials and microorganisms and to separate the microorganisms from the bioactive compounds. For the purposes of this patent application, bioactive compounds are defined as those biochemical compounds of microbial origin which consist of many different types of molecular structures.

In one embodiment, the clarified liquid containing the bioactive compounds is mixed with a saturated solution of ammonium sulfate to precipitate out proteins and other bioactive compounds. The precipitate is concentrated by centrifugation and separated from the remaining solution, re-dissolved in sterile phosphate buffer, and treated by dialysis to remove ammonium sulfate. The precipitate is then fractionated by size exclusion chromatography to obtain seven fractions.

Fractions 1, 2, 4 and 6 are separated from the remaining three fractions. Each of these fractions, when applied to the soil, either individually or in combinations thereof, generates a growth response in the plants that are planted in the treated soil. The materials in the fractions stimulate plant growth, including but not limited to root growth, shoot growth, number of blooms per plant, number of fruit from each plant, and overall size.

In one embodiment of the invention, fractions 1, 2, 4 and 6 are individually diluted with water prior to application to soil. In another embodiment of the invention, fractions 1, 2, 4 and 6 are combined together in different combinations prior to dilution.

The diluted fraction or fractions are applied to the soil by hand, by sprayers or by plane.

In another embodiment the diluted fractions are mixed with other nutrients, fertilizers, or compounds that promote plant growth or improve the quality of the soil, prior to dilution or application.

In another embodiment, the fractions are freeze dried and subsequently re-dissolved in an aqueous solution prior to application to the soil.

In another embodiment, the fractions are spray dried and subsequently re-dissolved in an aqueous solution prior to application to the soil.

DETAILED DESCRIPTION

SuperBio SoilBuilder® is a commercially available product to be applied to the soil to promote plant growth and improve the quality of the soil and is sold to the general public through AMS and its licensees in both the United States and around the world. SuperBio SoilBuilder® is the starting point for the present invention. Anyone desiring a sample of Super-Bio SoilBuilder® can contact AMS or its licensees to purchase such sample.

In one embodiment of the invention, microorganisms are separated from SuperBio SoilBuilder® by filtration using sterile 0.45 and 0.022 μm membrane filters or by centrifugation at sufficient rpm to form a pellet and clarify the solution. Filtration and centrifugation removes suspended materials and microorganisms, including bacteria, and results in a clarified liquid which contains only bioactive compounds.

The clarified liquid is mixed with a saturated solution of ammonium sulfate, allowing bioactive compounds to precipitate out of the clarified liquid. The precipitate of bioactive compounds is recovered by use of centrifugation. The precipitate will result in a pellet. The use of saturated solution of ammonium sulfate is known in the art to precipitate and separate out proteins from other compounds.

The pellet or subsequently derived powder of the precipitate is re-dissolved in sterile phosphate buffer and treated by dialysis to remove the ammonium sulfate and equilibrate in phosphate buffered saline ("PBS"). The resulting solution is then fractionated by size exclusion chromatography. One such method of chromatography which can perform the size exclusion separations is the Superdex 200 column having a molecular size range of about 200 kDa to about 1.5 kDa. The column eluate extracts are obtained over time and combined into seven fractions from the ninety (90) originally obtained.

Figure 1:
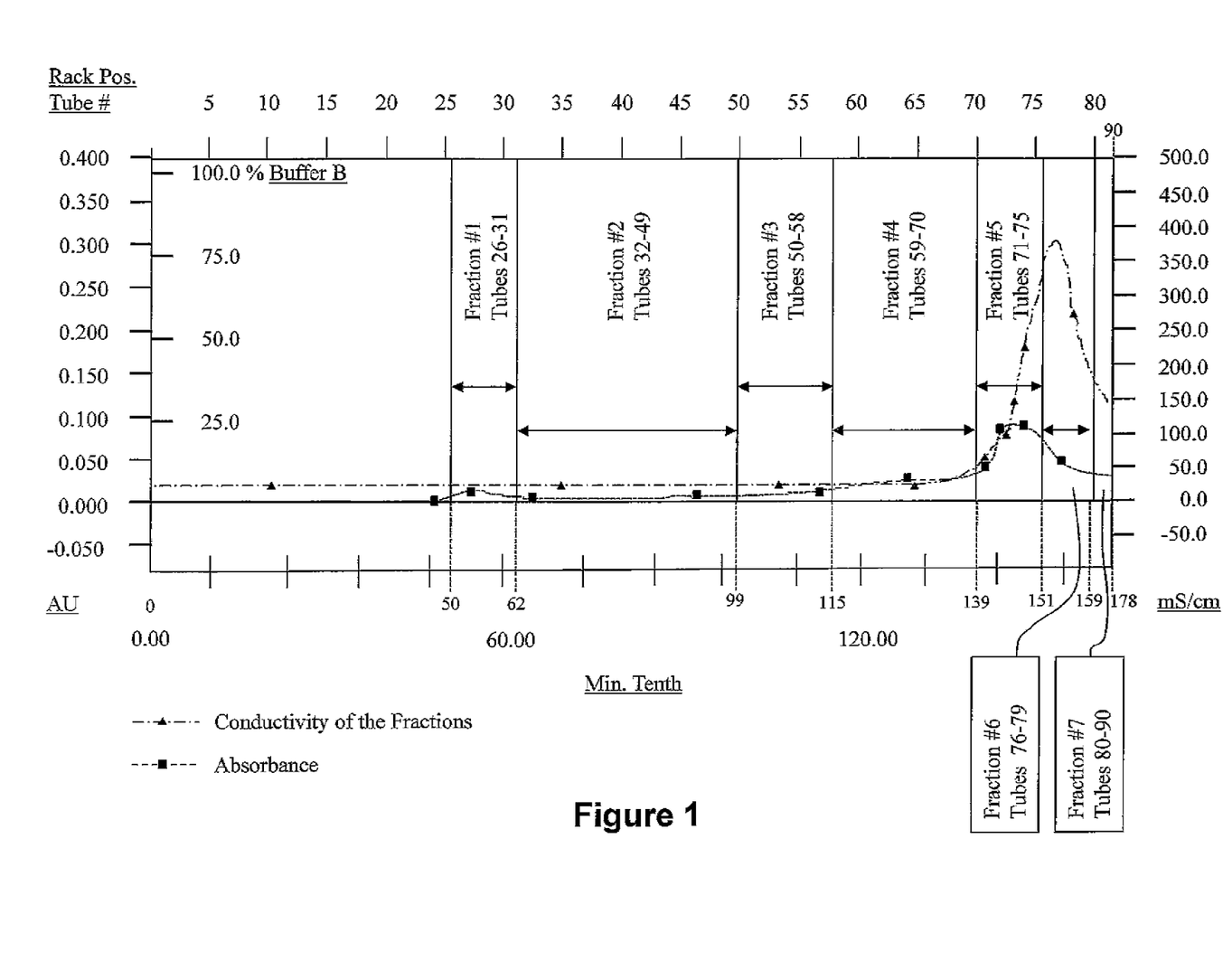
FIG. 1 is the graph chromatography results for the seven sample fractions.

FIG. 1 illustrates the seven fractions resulting from the size exclusion chromatography. The graphed curves illustrate the conductivity, measured in milliSiemens per centimeter (mS/cm), and the absorbance, measured in absorbance units (AU), of the seven fractions. The absorbance of each fraction is the amount of light absorbed by each fraction at a wavelength of 280 nanometers.

Fraction 1 encompasses the materials collected in tubes 26 through 31 having an elution time range of about 50 minute tenths to about 62 minute tenths, a conductivity range of about 8 mS/cm to about 15 mS/cm, an absorbance range of about 0.009 AU to about 0.017 AU, and contains the largest compounds.

Fraction 2 encompasses the materials collected in tubes 32 through 49 having an elution time range of about 62 minute tenths to about 99 minute tenths, a conductivity range of about 5 mS/cm to about 10 mS/cm, an absorbance range of about 0.005 AU to about 0.010 AU, and contains the next smallest compounds.

Fraction 3 encompasses the materials collected in tubes 50 through 58 having an elution time range of about 99 minute tenths to about 115 minute tenths, a conductivity range of about 10 mS/cm to about 20 mS/cm, an absorbance range of about 0.010 AU to about 0.018 AU, and contains the next smallest compounds.

Fraction 4 encompasses the materials collected in tubes 59 through 70 having an elution time range of about 115 minute tenths to about 139 minute tenths, a conductivity range of about 20 mS/cm to about 40 mS/cm, an absorbance range of about 0.018 AU to about 0.030 AU, and contains the next smallest compounds.

Fraction 5 encompasses the materials collected in tubes 71 through 75 having an elution time range of about 139 minute tenths to about 151 minute tenths, a conductivity range of about 40 mS/cm to about 350 mS/cm, an absorbance range of about 0.030 AU to about 0.090 AU, and contains the next smallest compounds.

Fraction 6 encompasses the materials collected in tubes 76 through 79 having an elution time range of about 151 minute tenths to about 159 minute tenths, a conductivity range of about 180 mS/cm to about 380 mS/cm, an absorbance range of about 0.030 AU to about 0.080 AU, and contains the next smallest compounds.

Fraction 7 encompasses the materials collected in tubes 80 through 90 having an elution time range of about 159 minute tenths to about 178 minute tenths, a conductivity range of about 145 mS/cm to about 180 mS/cm, an absorbance range of about 0.025 AU to about 0.030 AU, and contains the smallest compounds.

The molecular size range of the compounds in each fraction is calculated using the molecular range for the fractions (about 200 kDa to about 1.5 kDa) and the total number of tubes for the fractions (tubes 26 to 90). The results are in Table 1 below.

TABLE 1

| Fraction No. | Tube No. Range | Elution Time (minute tenths) | Approximate Molecular Size Range (kDa) |
|---|---|---|---|
| 1 | 26-31 | 50-62 | 187-200 |
| 2 | 32-49 | 62-99 | 128-187 |

TABLE 1-continued

| Fraction No. | Tube No. Range | Elution Time (minute tenths) | Approximate Molecular Size Range (kDa) |
|---|---|---|---|
| 3 | 50-58 | 99-115 | 100-128 |
| 4 | 59-70 | 115-139 | 63-100 |
| 5 | 71-75 | 139-151 | 48-63 |
| 6 | 76-79 | 151-159 | 35-48 |
| 7 | 80-90 | 159-178 | 1.5-35 |

Fractions 1, 2, 4 and 6 are separated from the remaining three fractions. Each of these fractions, when applied to the soil, either individually or in combinations thereof, generates a plant growth response in the plants that are in the treated soil. The materials in the fractions stimulate plant growth, including but not limited to root growth, shoot growth, number of blooms per plant, number of fruit from each plant, and overall size.

The seven fractions were analyzed by SDS-PAGE (sodium dodecyl sulfate polyacrylamide gel electrophoresis) and treated with a coomassie stain to confirm size fractionation and the presence of proteins. Even though the separation method used is intended to precipitate out proteins and it was anticipated that proteins would be found, proteins were not identified or observed in the fractions. This result was confirmed by the use of UV scans and mass spectrometry and no proteins were identified in fractions 1, 2, 4 and 6. This was a surprising result. It is possible that proteins or peptides were either at levels below the detection limits of a Bradford Dye test or other compounds or buffers in the test solution interfered with detection.

In one embodiment of the invention, fractions 1, 2, 4 and 6 are individually diluted with water prior to application to soil. Fraction 1 is diluted in the range of about 1:300 to 1:400 by volume. Fraction 2 is diluted in the range of about 1:100 to 1:200 by volume. Fraction 4 is diluted in the range of about 1:100 to 1:200 by volume. Fraction 6 is diluted in the range of about 1:500 to 1:600 by volume.

In another embodiment of the invention, fractions 1, 2, 4 and 6 are combined together prior to dilution. When fractions 1 and 2 are combined, they are diluted in the range of about 1:50 to 1:150 by volume. When fractions 1 and 4 are combined, they are diluted in the range of about 1:100 to 1:200 by volume. When fractions 1 and 6 are combined, they are diluted in the range of about 1:200 to 1:300 by volume. When fractions 2 and 4 are combined, they are diluted in the range of about 1:50 to 1:150 by volume. When fractions 2 and 6 are combined, they are diluted in the range of about 1:50 to 1:150 by volume. When fractions 4 and 6 are combined, they are diluted in the range of about 1:100 to 1:200 by volume. When fractions 1, 2, and 4 are combined, they are diluted in the range of about 1:25 to 1:125 by volume. When fractions 1, 2, and 6 are combined, they are diluted in the range of about 1:50 to 1:150 by volume. When fractions 1, 4, and 6 are combined, they are diluted in the range of about 1:50 to 1:150 by volume. When fractions 2, 4, and 6 are combined, they are diluted in the range of about 1:50 to 1:150 by volume. When fractions 1, 2, 4, and 6 are combined, they are diluted in the range of about 1:15 to 1:115 by volume.

The diluted fraction or fractions are then applied to the soil. The diluted fractions or fractions can be applied by hand, by sprayer located on the ground or by plane or overhead sprayers.

The fractions can be mixed with other nutrients, fertilizers, or compounds that promote plant growth or improve the quality of the soil, prior to dilution or application.

The application rate per acre of the fraction after dilution is about 1 to 2 gallons per acre.

Fractions 1, 2, 4, and 6 can also be freeze dried or spray dried by techniques known in the art. This is possible since fractions 1, 2, 4, and 6 do not contain any microorganisms that would be killed during the freeze drying or spray drying processes.

Further, since fractions 1, 2, 4, and 6 do not contain microorganisms, the products have a longer shelf life and do not require storage conditions necessary to keep microorganisms alive.

Freeze drying and spray drying allows for easier transportation and storage. The fractions which have been freeze dried or spray dried will be re-hydrated during the dilution process.

The growth response is not limited to a single type of plant or specific genus of plants.

EXAMPLE ONE

One example of effectiveness of fractions on pepper plants to stimulate plant growth is documented below. Pepper plants were chosen since they are representative of important agricultural crops. The growth response documented with pepper plants would be representative of other plant species.

Pepper plants were grown from seeds and selected for uniformity of transplant size. Five plants were used for each of the four fractions, the original SuperBio SoilBuilder®, and a control. The pepper plants were transplanted into six-inch pots with 1800 $cm^3$ of potting soil.

Each fraction was individually diluted to create 500 mL of solution. The amount of fraction 1 diluted was 1.3 mL. The amount of fraction 2 diluted was 4.2 mL. The amount of fraction 4 diluted was 2.9 mL. The amount of fraction 6 diluted was 0.9 mL. The amount of SoilBuilder® diluted was 15.0 mL. The control was 500 mL of water.

After each plant was transplanted, 100 mL of the respective solution was applied evenly around the base of the respective plant. Water and the same fertilizer were applied to all the pepper plants in the same quantity on a weekly basis. The fertilizer used was Scotts, Peters Professional Pete-Lite Special water soluble fertilizer (20-10-20) with trace nutrients and was dissolved in water at 1 pound/100 gallons (454 g/378.5 L).

Plants were harvested approximately 35 days after transplanting. Fresh roots and shoots, dry roots and shoots, number of blooms, and number of fruit were measured. The resulting means from the measurements of the five plants per treatment are in Table 2 below.

TABLE 2

| Treatment | Root Fresh Wt. (g) | Shoot Fresh Wt. (g) | Total Fresh Wt. (g) | Dry Root Wt. (g) | Dry Shoot Wt. (g) | Total Dry Wt. (g) | No. of Blooms | No. of Fruit |
|---|---|---|---|---|---|---|---|---|
| Fraction 1 | 20.70a | 35.30ab | 55.99ab | 1.65a | 4.00ab | 5.65ab | 3.00abc | 2.00ab |
| Fraction 2 | 19.42abc | 34.18bc | 53.60abc | 1.50abc | 3.73bc | 5.23bcd | 2.60bc | 1.00b |
| Fraction 4 | 19.18abc | 38.24a | 57.42a | 1.58abc | 4.28a | 5.86a | 4.40a | 3.00a |

TABLE 2-continued

| Treatment | Root Fresh Wt. (g) | Shoot Fresh Wt. (g) | Total Fresh Wt. (g) | Dry Root Wt. (g) | Dry Shoot Wt. (g) | Total Dry Wt. (g) | No. of Blooms | No. of Fruit |
|---|---|---|---|---|---|---|---|---|
| Fraction 6 | 19.49ab | 31.50cd | 50.99bcd | 1.65a | 3.89abc | 5.54abc | 2.80abc | 1.40b |
| SuperBio SoilBuilder ® | 18.48abc | 32.82bcd | 51.30bcd | 1.44abc | 3.76bc | 5.20bcd | 2.20c | 1.2b |
| Control | 16.9bc | 30.49d | 47.40d | 1.41bc | 3.67bc | 5.08bcd | 4.0ab | 1.6ab |
| $LSD_{0.05}$ | 2.88 | 3.34 | 5.33 | 0.238 | 0.40 | .058 | 1.65 | 1.42 |

Results followed by the same letter within a column are not significantly different at P = 0.05.

These results show that the individualized fractions perform better once isolated than in the original SuperBio SoilBuilder® product, which included the three remaining fractions and the suspended materials and microorganisms. It is further evidenced that fractions 1 and 6 are most stimulatory for root growth and fractions 1 and 4 were most stimulatory for shoot growth.

The effects of the materials in fractions 1, 2, 4, and 6 are sustained. These fractions were tested again six months after fractionization. The fractions were kept refrigerated at 4° C. since fractionization. This additional example documents the long-term effects of bioactive compounds in these fractions.

EXAMPLE 2

Pepper plants were grown from seeds and thirty plants were selected based on uniformity of transplant size. Five plants were used for each of fractions 1, 2, 4, and 6, the SuperBio SoilBuilder®, and a control. The pepper plants were transplanted into six-inch pots with 1800 cm³ of potting soil.

Each of the fractions and the SuperBio SoilBuilder® were individually diluted to create 500 mL of solution for application to the pepper plants. The amount of fraction 1 diluted was 1.3 mL. The amount of fraction 2 diluted was 4.2 mL. The amount of fraction 4 diluted was 2.9 mL. The amount of fraction 6 diluted was 0.9 mL. The amount of SoilBuilder®diluted was 15.0 mL. The control was 500 mL of water.

After the first group of five pepper plants was transplanted, 100 mL of fraction 1 diluted solution was applied evenly around the base of each of the five plants. After the second group of five pepper plants was transplanted, 100 mL of fraction 2 diluted solution was applied evenly around the base of each of the five plants. After the third group of five pepper plants was transplanted, 100 mL of fraction 4 diluted solution was applied evenly around the base of each of the five plants. After the fourth group of five pepper plants was transplanted, 100 mL of fraction 6 diluted solution was applied evenly around the base of each of the five plants. After the fifth group of five pepper plants was transplanted, 100 mL of the diluted SuperBio SoilBuilder® solution was applied evenly around the base of each of the five plants. After the sixth group of five pepper plants was transplanted, 100 mL of the control water was applied evenly around the base of each of the five plants.

Water and the same fertilizer were applied to all the pepper plants in the same quantity on a weekly basis. As with example 1, the fertilizer used was Scotts, Peters Professional Pete-Lite Special water soluble fertilizer (20-10-20) with trace nutrients and was dissolved in water at 1 pound/100 gallons (454 g/378.5 L).

Twenty-nine days after transplanting and application of solutions, the number of first blooms was counted. The averages of first blooms per plant per treatment are given in Table 3 below.

TABLE 3

| Treatment | Average number of blooms per treatment |
|---|---|
| Fraction 1 | 2.8** |
| Fraction 2 | 2.6** |
| Fraction 4 | 2.4** |
| Fraction 6 | 2.8** |
| SuperBio SoilBuilder ® | 2.6** |
| Control | 0.4 |
| $LSD_{0.01}$ | 1.3 |

**Indicates a significantly higher measurement compared to control at P = 0.01

Plants were harvested approximately 43 days after transplanting. Average number of blooms, average number of fruit, average weight of fruit, height, weight of fresh shoots, and weight of fresh roots was determined. The resulting average measures for the fresh roots and shoots, dry roots and shoots, number of blooms, and number of fruit were measured are given in Table 4 below.

TABLE 4

| Treatment | Root Fresh Wt. (g) | Shoot Fresh Wt. (g) | Height (cm) | Average number of blooms | Average number of fruit | Average fruit weight (g) |
|---|---|---|---|---|---|---|
| Fraction 1 | 28.6 | 70.74 | 41.4 | 7.8* | 3.6* | 36.3* |
| Fraction 2 | 34.3* | 90.10* | 47.2* | 9.2* | 3.6* | 33.1* |
| Fraction 4 | 36.4* | 89.42* | 45.0 | 7.0 | 3.8* | 35.5* |
| Fraction 6 | 31.2 | 74.34 | 45.6 | 6.2 | 2.8 | 42.3* |
| SuperBio SoilBuilder ® | 34.5* | 71.94 | 42.8 | 6.8 | 4.2* | 48.7* |
| Control | 25.7 | 67.62 | 43.4 | 4.8 | 1.8 | 10.6 |
| $LSD_{0.05}$ | 5.7 | 13.40 | 3.7 | 2.6 | 1.1 | 9.2 |

*Indicates a significantly higher measurement compared to control at P = 0.05

Figure 2:
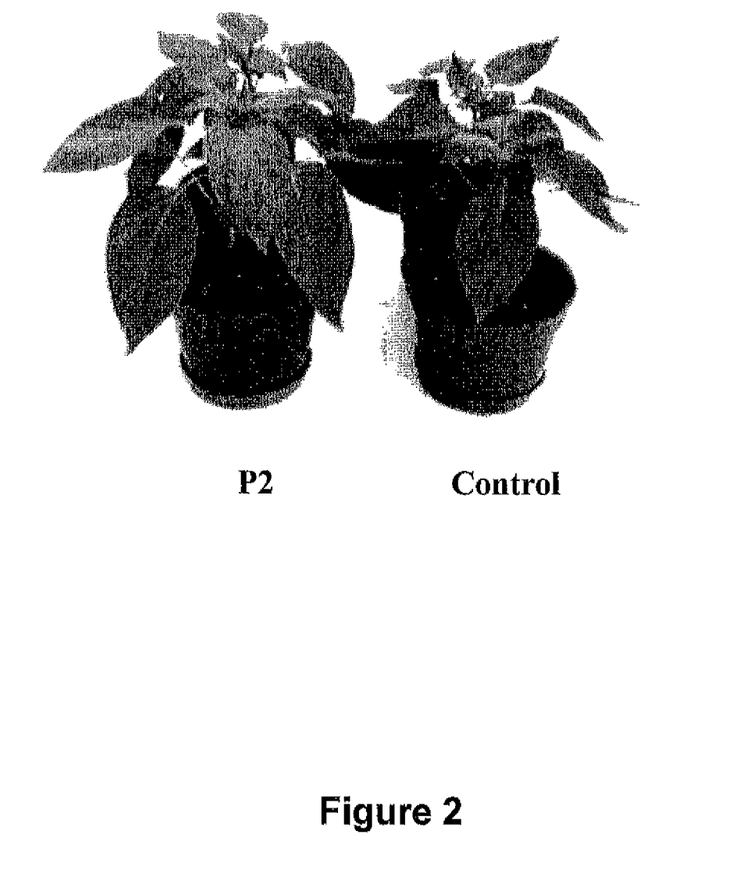
FIG. 2 is photograph of results caused by use of invention.

Pictures of a representative pepper plant to which fraction 2 diluted solution was applied and a pepper plant to which the control solution was applied is shown in FIG. 2.

Figure 3:
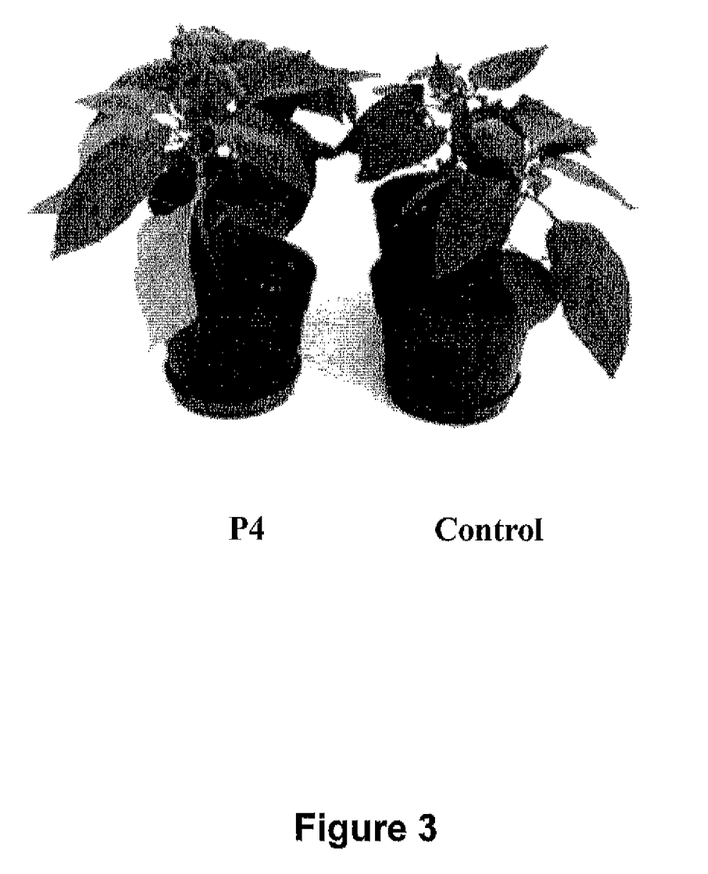
FIG. 3 is photograph of results caused by use of invention.

Pictures of a representative pepper plant to which fraction 4 dilution solution was applied and a pepper plant to which the control solution was applied is shown in FIG. 3.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:
1. A method of isolating bioactive compounds comprising:
apportioning an amount of a fermentation extract solution;
removing biological matter resulting in a clarified liquid;
mixing the clarified liquid with an ammonium sulfate solution resulting in a precipitate;

isolating the precipitate by centrifugation;
redissolving the precipitate in a phosphate buffer;
fractionizing the redissolved precipitate into seven fractions, each fraction sequentially decreasing in compound size;
removing a set of one or more chosen fractions of the seven fractions; and,
applying the set of one or more chosen fractions to a portion of soil media adjacent a plant.

2. The method of isolating bioactive compounds of claim 1, wherein the step of fractionizing comprises fractionizing the precipitate with size exclusion chromatography, where the molecular size range is about 1.5 kDa to about 200 kDa.

3. The method of isolating bioactive compounds of claim 2, wherein the step of removing a set of one or more chosen fractions further comprises removing a fraction having a molecular size range of about 187 kDa to about 200 kDa.

4. The method of isolating bioactive compounds of claim 3, further comprising the step of diluting the fraction with water in a range of about 1:300 to about 1:400 by volume prior to the step of applying the fraction.

5. The method of isolating bioactive compounds of claim 2, wherein the step of removing a set of one or more chosen fractions further comprises removing a fraction having a molecular size range of about 128 kDa to about 187 kDa.

6. The method of isolating bioactive compounds of claim 5, further comprising the step of diluting the fraction with water in a range of about 1:100 to about 1:200 by volume prior to the step of applying the fraction.

7. The method of isolating bioactive compounds of claim 2, wherein the step of removing a set of one or more chosen fractions further comprises removing a fraction having a molecular size range of about 63 kDa to about 100 kDa.

8. The method of isolating bioactive compounds of claim 7, further comprising the step of diluting the fraction with water in a range of about 1:100 to about 1:200 by volume prior to the step of applying the fraction.

9. The method of isolating bioactive compounds of claim 2, wherein the step of removing a set of one or more chosen fractions further comprises removing a fraction having a molecular size range of about 35 kDa to about 48 kDa.

10. The method of isolating bioactive compounds of claim 9, further comprising the step of diluting the fraction with water in a range of about 1:500 to about 1:600 by volume prior to the step of applying the fraction.

11. The method of isolating bioactive compounds of claim 2, wherein the step of removing a set of one or more chosen fractions further comprises removing a primary fraction having a molecular size range of about 187 kDa to about 200 kDa and a secondary fraction having a molecular size range of about 128 kDa to about 187 kDa.

12. The method of isolating bioactive compounds of claim 11, further comprising the steps of:
combining the primary fraction and the secondary fraction into a combined fraction; and
diluting the combined fraction with water in a range of about 1:50 to about 1:150 by volume prior to the step of applying the fraction.

13. The method of isolating bioactive compounds of claim 2, wherein the step of removing a set of one or more chosen fractions further comprises removing a primary fraction having a molecular size range of about 187 kDa to about 200 kDa and a secondary fraction having a molecular size range of about 63 kDa to about 100 kDa.

14. The method of isolating bioactive compounds of claim 13, further comprising the steps of:
combining the primary fraction and the secondary fraction into a combined fraction; and
diluting the combined fraction with water in a range of about 1:100 to about 1:200 by volume prior to the step of applying the fraction.

15. The method of isolating bioactive compounds of claim 2, wherein the step of removing a set of one or more chosen fractions further comprises removing a primary fraction having a molecular size range of about 187 kDa to about 200 kDa and a secondary fraction having a molecular size range of about 35 kDa to about 48 kDa.

16. The method of isolating bioactive compounds of claim 15, further comprising the steps of:
combining the primary fraction and the secondary fraction into a combined fraction; and
diluting the combined fraction with water in a range of about 1:200 to about 1:300 by volume prior to the step of applying the fraction.

17. The method of isolating bioactive compounds of claim 2, wherein the step of removing a set of one or more chosen fractions further comprises removing a primary fraction having a molecular size range of about 128 kDa to about 187 kDa and a secondary fraction having a molecular size range of about 63 kDa to about 100 kDa.

18. The method of isolating bioactive compounds of claim 17, further comprising the steps of:
combining the primary fraction and the secondary fraction into a combined fraction; and
diluting the combined fraction with water in a range of about 1:50 to about 1:150 by volume prior to the step of applying the fraction.

19. The method of isolating bioactive compounds of claim 2, wherein the step of removing a set of one or more chosen fractions further comprises removing a primary fraction having a molecular size range of about 128 kDa to about 187 kDa and a secondary fraction having a molecular size range of about 35 kDa to about 48 kDa.

20. The method of isolating bioactive compounds of claim 19, further comprising the steps of:
combining the primary fraction and the secondary fraction into a combined fraction; and
diluting the combined fraction with water in a range of about 1:50 to about 1:150 by volume prior to the step of applying the fraction.

21. The method of isolating bioactive compounds of claim 2, wherein the step of removing a set of one or more chosen fractions further comprises removing a primary fraction having a molecular size range of about 63 kDa to about 100 kDa and a secondary fraction having a molecular size range of about 35 kDa to about 48 kDa.

22. The method of isolating bioactive compounds of claim 21, further comprising the steps of:
combining the primary fraction and the secondary fraction into a combined fraction; and
diluting the combined fraction with water in a range of about 1:100 to about 1:200 by volume prior to the step of applying the fraction.

23. The method of isolating bioactive compounds of claim 2, wherein the step of removing a set of one or more chosen fractions further comprises removing a primary fraction having a molecular size range of about 187 kDa to about 200 kDa, a secondary fraction having a molecular size range of about 128 kDa to about 187 kDa, and a tertiary fraction having a molecular size range of about 63 kDa to about 100 kDa.

24. The method of isolating bioactive compounds of claim 23, further comprising the steps of:
   combining the primary fraction, the secondary fraction, and the tertiary fraction into a combined fraction; and
   diluting the combined fraction with water in a range of about 1:25 to about 1:125 by volume prior to the step of applying the fraction.

25. The method of isolating bioactive compounds of claim 2, wherein the step of removing a set of one or more chosen fractions further comprises removing a primary fraction having a molecular size range of about 187 kDa to about 200 kDa, a secondary fraction having a molecular size range of about 128 kDa to about 187 kDa, and a tertiary fraction having a molecular size range of about 35 kDa to about 48 kDa.

26. The method of isolating bioactive compounds of claim 25, further comprising the steps of:
   combining the primary fraction, the secondary fraction, and the tertiary fraction into a combined fraction; and
   diluting the combined fraction with water in a range of about 1:50 to about 1:150 by volume prior to the step of applying the fraction.

27. The method of isolating bioactive compounds of claim 2, wherein the step of removing a set of one or more chosen fractions further comprises removing a primary fraction having a molecular size range of about 187 kDa to about 200 kDa, a secondary fraction having a molecular size range of about 63 kDa to about 100 kDa, and a tertiary fraction having a molecular size range of about 35 kDa to about 48 kDa.

28. The method of isolating bioactive compounds of claim 27, further comprising the steps of:
   combining the primary fraction, the secondary fraction, and the tertiary fraction into a combined fraction; and
   diluting the combined fraction with water in a range of about 1:50 to about 1:150 by volume prior to the step of applying the fraction.

29. The method of isolating bioactive compounds of claim 2, wherein the step of removing a set of one or more chosen fractions further comprises removing a primary fraction having a molecular size range of about 128 kDa to about 187 kDa, a secondary fraction having a molecular size range of about 63 kDa to about 100 kDa, and a tertiary fraction having a molecular size range of about 35 kDa to about 48 kDa.

30. The method of isolating bioactive compounds of claim 29, further comprising the steps of:
   combining the primary fraction, the secondary fraction, and the tertiary fraction into a combined fraction; and
   diluting the combined fraction with water in a range of about 1:50 to about 1:150 by volume prior to the step of applying the fraction.

31. The method of isolating bioactive compounds of claim 2, wherein the step of removing a set of one or more chosen fractions further comprises removing a primary fraction having a molecular size range of about 187 kDa to about 200 kDa, a secondary fraction having a molecular size range of about 128 kDa to about 187 kDa, a tertiary fraction having a molecular size range of about 63 kDa to about 100 kDa, and a quaternary fraction having a molecular size range of about 35 kDa to about 48 kDa.

32. The method of isolating bioactive compounds of claim 31, further comprising the steps of:
   combining the primary fraction, the secondary fraction, the tertiary fraction, and the quaternary fraction into a combined fraction; and
   diluting the combined fraction with water in a range of about 1:15 to about 1:115 by volume prior to the step of applying the fraction.

33. The method of isolating bioactive compounds of claim 1, further comprising the step of freeze drying the set of one or more chosen fractions.

34. The method of isolating bioactive compounds of claim 1, further comprising the step of spray drying the set of one or more chosen fractions.

35. The method of isolating bioactive compounds of claim 1, further comprising removing the biological matter by filtration.

36. The method of isolating bioactive compounds of claim 1, further comprising removing the biological matter by centrifugation.

37. The method of isolating bioactive compounds of claim 1, further comprising the step of removing ammonium sulfate from the precipitate by dialysis.

38. The method of isolating bioactive compounds of claim 1, comprising an initial step of obtaining the fermentation extract solution from a commercial product selected from the group of SuperBio SoilBuilder® solution, SuperBio Ag Blend® solution, SuperBio SoilLife™ solution, and NutriLife® solution.

39. The method of isolating bioactive compounds of claim 1, wherein the step of fractionizing the redissolved precipitate comprises fractionizing the redissolved precipitate by size exclusion chromatography, where the molecular size range is about 1.5 kDa to about 200 kDa; and fractionizing the redissolved precipitate into:
   a first fraction having a molecular size range of about 187 kDa to about 200 kDa;
   a second fraction having a molecular size range of about 128 kDa to about 187 kDa;
   a third fraction having a molecular size range of about 100 kDa to about 128 kDa;
   a fourth fraction having a molecular size range of about 63 kDa to about 100 kDa;
   a fifth fraction having a molecular size range of about 48 kDa to about 63 kDa;
   a sixth fraction having a molecular size range of about 35 kDa to about 48 kDa; and
   a seventh fraction having a molecular size range of about 1.5 kDa to about 35 kDa.

40. A method of isolating bioactive compounds comprising:
   apportioning an amount of a fermentation extract solution;
   removing biological matter resulting in a clarified liquid;
   mixing the clarified liquid with an ammonium sulfate solution resulting in a precipitate;
   isolating the precipitate by centrifugation;
   redissolving the precipitate in a phosphate buffer;
   fractionizing the redissolved precipitate into seven fractions, each fraction sequentially decreasing in compound size;
   removing a set of one or more chosen fractions of the seven fractions; and,
   applying the set of one or more chosen fractions to a portion of soil media adjacent a plant.

41. The method of isolating bioactive compounds of claim 40, wherein the step of fractionizing comprises fractionizing the precipitate with size exclusion chromatography, where the molecular size range is about 1.5 kDa to about 200 kDa.

42. The method of isolating bioactive compounds of claim 41, wherein the step of removing a set of one or more chosen fractions further comprises removing a fraction having a conductivity range of about 8 mS/cm to about 15 mS/cm.

43. The method of isolating bioactive compounds of claim 41, wherein the step of removing a set of one or more chosen fractions further comprises removing a fraction having a conductivity range of about 5 mS/cm to about 10 mS/cm.

44. The method of isolating bioactive compounds of claim 41, wherein the step of removing a set of one or more chosen fractions further comprises removing a fraction having a conductivity range of about 20 mS/cm to about 40 mS/cm.

45. The method of isolating bioactive compounds of claim 41, wherein the step of removing a set of one or more chosen fractions further comprises removing a fraction having a conductivity range of about 180 mS/cm to about 380 mS/cm.

46. The method of isolating bioactive compounds of claim 41, wherein the step of removing a set of one or more chosen fractions further comprises removing a primary fraction having a conductivity range of about 8 mS/cm to about 15 mS/cm and a secondary fraction having a conductivity range of about 5 mS/cm to about 10 mS/cm.

47. The method of isolating bioactive compounds of claim 41, wherein the step of removing a set of one or more chosen fractions further comprises removing a primary fraction having a conductivity range of about 8 mS/cm to about 15 mS/cm and a secondary fraction having a conductivity range of about 20 mS/cm to about 40 mS/cm.

48. The method of isolating bioactive compounds of claim 41, wherein the step of removing a set of one or more chosen fractions further comprises removing a primary fraction having a conductivity range of about 8 mS/cm to about 15 mS/cm and a secondary fraction having a conductivity range of about 180 mS/cm to about 380 mS/cm.

49. The method of isolating bioactive compounds of claim 41, wherein the step of removing a set of one or more chosen fractions further comprises removing a primary fraction having a conductivity range of about 5 mS/cm to about 10 mS/cm and a secondary fraction having a conductivity range of about 20 mS/cm to about 40 mS/cm.

50. The method of isolating bioactive compounds of claim 41, wherein the step of removing a set of one or more chosen fractions further comprises removing a primary fraction having a conductivity range of about 5 mS/cm to about 10 mS/cm and a secondary fraction having a conductivity range of about 180 mS/cm to about 380 mS/cm.

51. The method of isolating bioactive compounds of claim 41, wherein the step of removing a set of one or more chosen fractions further comprises removing a primary fraction having a conductivity range of about 20 mS/cm to about 40 mS/cm and a secondary fraction having a conductivity range of about 180 mS/cm to about 380 mS/cm.

52. The method of isolating bioactive compounds of claim 41, wherein the step of removing a set of one or more chosen fractions further comprises removing a primary fraction having a conductivity range of about 8 mS/cm to about 15 mS/cm, a secondary fraction having a conductivity range of about 5 mS/cm to about 10 mS/cm, and a tertiary fraction having a conductivity range of about 20 mS/cm to about 40 mS/cm.

53. The method of isolating bioactive compounds of claim 41, wherein the step of removing a set of one or more chosen fractions further comprises removing a primary fraction having a conductivity range of about 8 mS/cm to about 15 mS/cm, a secondary fraction having a conductivity range of about 5 mS/cm to about 10 mS/cm, and a tertiary fraction having a conductivity range of about 180 mS/cm to about 380 mS/cm.

54. The method of isolating bioactive compounds of claim 41, wherein the step of removing a set of one or more chosen fractions further comprises removing a primary fraction having a conductivity range of about 8 mS/cm to about 15 mS/cm, a secondary fraction having a conductivity range of about 20 mS/cm to about 40 mS/cm, and a tertiary fraction having a conductivity range of about 180 mS/cm to about 380 mS/cm.

55. The method of isolating bioactive compounds of claim 41, wherein the step of removing a set of one or more chosen fractions further comprises removing a primary fraction having a conductivity range of about 5 mS/cm to about 10 mS/cm, a secondary fraction having a conductivity range of about 20 mS/cm to about 40 mS/cm, and a tertiary fraction having a conductivity range of about 180 mS/cm to about 380 mS/cm.

56. The method of isolating bioactive compounds of claim 41, wherein the step of removing a set of one or more chosen fractions further comprises removing a primary fraction having a conductivity range of about 8 mSkm to about 15 mS/cm, a secondary fraction having a conductivity range of about 5 mS/cm to about 10 mS/cm, a tertiary fraction having a conductivity range of about 20 mS/cm to about 40 mS/cm, and a quaternary fraction having a conductivity range of about 180 mS/cm to about 380 mS/cm.

57. The method of isolating bioactive compounds of claim 40, further comprising the step of freeze drying the set of one or more chosen fractions.

58. The method of isolating bioactive compounds of claim 40, further comprising the step of spray drying the set of one or more chosen fractions.

59. The method of isolating bioactive compounds of claim 40, further comprising removing the biological matter by filtration.

60. The method of isolating bioactive compounds of claim 40, further comprising removing the biological matter by centrifugation.

61. The method of isolating bioactive compounds of claim 40, further comprising the step of removing ammonium sulfate from the precipitate by dialysis.

62. The method of isolating bioactive compounds of claim 40, comprising an initial step of obtaining the fermentation extract solution from a commercial product selected from the group of SuperBio SoilBuilder® solution, SuperBio Ag Blend® solution, SuperBio SoilLife™ solution, and NutriLife® solution.

63. The method of isolating bioactive compounds of claim 40, wherein the step of fractionizing the redissolved precipitate comprises fractionizing the redissolved precipitate by size exclusion chromatography, where the molecular size range is about 1.5 kDa to about 200 kDa; and fractionizing the redissolved precipitate into:
    a first fraction having a conductivity range of about 8 mS/cm to about 15 mS/cm;
    a second fraction having a conductivity range of about 5 mS/cm to about 10 mS/cm;
    a third fraction having a conductivity range of about 10 mS/cm to about 20 mS/cm;
    a fourth fraction having a conductivity range of about 20 mS/cm to about 40 mS/cm;
    a fifth fraction having a conductivity range of about 40 mS/cm to about 350 mS/cm;
    a sixth fraction having a conductivity range of about 180 mS/cm to about 380 mS/cm; and
    a seventh fraction having a conductivity range of about 145 mS/cm to about 180 mS/cm.

64. A method of isolating bioactive compounds comprising:
    apportioning an amount of a fermentation extract solution;
    removing biological matter resulting in a clarified liquid;
    mixing the clarified liquid with an ammonium sulfate solution resulting in a precipitate;

isolating the precipitate by centrifugation;
redissolving the precipitate in a phosphate buffer;
fractionizing the redissolved precipitate into seven fractions, each fraction sequentially decreasing in compound size;
removing a set of one or more chosen fractions of the seven fractions; and,
applying the set of one or more chosen fractions to a portion of soil media adjacent a plant.

65. The method of isolating bioactive compounds of claim 64, wherein the step of fractionizing comprises fractionizing the precipitate with size exclusion chromatography, where the molecular size range is about 1.5 kDa to about 200 kDa.

66. The method of isolating bioactive compounds of claim 65, wherein the step of removing a set of one or more chosen fractions further comprises removing a fraction having an absorbance range of about 0.009 AU to about 0.017 AU.

67. The method of isolating bioactive compounds of claim 65, wherein the step of removing a set of one or more chosen fractions further comprises removing a fraction having an absorbance range of about 0.005 AU to about 0.010 AU.

68. The method of isolating bioactive compounds of claim 65, wherein the step of removing a set of one or more chosen fractions further comprises removing a fraction having an absorbance range of about 0.018 AU to about 0.030 AU.

69. The method of isolating bioactive compounds of claim 65, wherein the step of removing a set of one or more chosen fractions further comprises removing a fraction having an absorbance range of about 0.030 AU to about 0.080 AU.

70. The method of isolating bioactive compounds of claim 65, wherein the step of removing a set of one or more chosen fractions further comprises removing a primary fraction having an absorbance range of about 0.009 AU to about 0.017 AU and a secondary fraction having an absorbance range of about 0.005 AU to about 0.010 AU.

71. The method of isolating bioactive compounds of claim 65, wherein the step of removing a set of one or more chosen fractions further comprises removing a primary fraction having an absorbance range of about 0.009 AU to about 0.017 AU and a secondary fraction having an absorbance range of about 0.018 AU to about 0.030 AU.

72. The method of isolating bioactive compounds of claim 65, wherein the step of removing a set of one or more chosen fractions further comprises removing a primary fraction having an absorbance range of about 0.009 AU to about 0.017 AU and a secondary fraction having an absorbance range of about 0.030 AU to about 0.080 AU.

73. The method of isolating bioactive compounds of claim 65, wherein the step of removing a set of one or more chosen fractions further comprises removing a primary fraction having an absorbance range of about 0.005 AU to about 0.010 AU and a secondary fraction having an absorbance range of about 0.018 AU to about 0.030 AU.

74. The method of isolating bioactive compounds of claim 65, wherein the step of removing a set of one or more chosen fractions further comprises removing a primary fraction having an absorbance range of about 0.005 AU to about 0.010 AU and a secondary fraction having an absorbance range of about 0.030 AU to about 0.080 AU.

75. The method of isolating bioactive compounds of claim 65, wherein the step of removing a set of one or more chosen fractions further comprises removing a primary fraction having an absorbance range of about 0.018 AU to about 0.030 AU and a secondary fraction having an absorbance range of about 0.030 AU to about 0.080 AU.

76. The method of isolating bioactive compounds of claim 65, wherein the step of removing a set of one or more chosen fractions further comprises removing a primary fraction having an absorbance range of about 0.009 AU to about 0.017 AU, a secondary fraction having an absorbance range of about 0.005 AU to about 0.010 AU, and a tertiary fraction having an absorbance range of about 0.018 AU to about 0.030 AU.

77. The method of isolating bioactive compounds of claim 65, wherein the step of removing a set of one or more chosen fractions further comprises removing a primary fraction having an absorbance range of about 0.009 AU to about 0.017 AU, a secondary fraction having an absorbance range of about 0.005 AU to about 0.010 AU, and a tertiary fraction having an absorbance range of about 0.030 AU to about 0.080 AU.

78. The method of isolating bioactive compounds of claim 65, wherein the step of removing a set of one or more chosen fractions further comprises removing a primary fraction having an absorbance range of about 0.009 AU to about 0.017 AU, a secondary fraction having an absorbance range of about 0.018 AU to about 0.030 AU, and a tertiary fraction having an absorbance range of about 0.030 AU to about 0.080 AU.

79. The method of isolating bioactive compounds of claim 65, wherein the step of removing a set of one or more chosen fractions further comprises removing a primary fraction having an absorbance range of about 0.005 AU to about 0.010 AU, a secondary fraction having an absorbance range of about 0.018 AU to about 0.030 AU, and a tertiary fraction having an absorbance range of about 0.030 AU to about 0.080 AU.

80. The method of isolating bioactive compounds of claim 65, wherein the step of removing a set of one or more chosen fractions further comprises removing a primary fraction having an absorbance range of about 0.009 AU to about 0.017 AU, a secondary fraction having an absorbance range of about 0.005 AU to about 0.010 AU, a tertiary fraction having an absorbance range of about 0.018 AU to about 0.030 AU, and a quaternary fraction having an absorbance range of about 0.030 AU to about 0.080 AU.

81. The method of isolating bioactive compounds of claim 64, further comprising the step of freeze drying the set of one or more chosen fractions.

82. The method of isolating bioactive compounds of claim 64, further comprising the step of spray drying the set of one or more chosen fractions.

83. The method of isolating bioactive compounds of claim 64, further comprising removing the biological matter by filtration.

84. The method of isolating bioactive compounds of claim 64, further comprising removing the biological matter by centrifugation.

85. The method of isolating bioactive compounds of claim 64, further comprising the step of removing ammonium sulfate from the precipitate by dialysis.

86. The method of isolating bioactive compounds of claim 64, comprising an initial step of obtaining the fermentation extract solution from a commercial product selected from the group of SuperBio SoilBuilder® solution, SuperBio Ag Blend® solution, SuperBio SoilLife™ solution, and NutriLife® solution.

87. The method of isolating bioactive compounds of claim 64, wherein the step of fractionizing the redissolved precipitate comprises fractionizing the redissolved precipitate by size exclusion chromatography, where the molecular size range is about 1.5 kDa to about 200 kDa; and fractionizing the redissolved precipitate into:

a first fraction having an absorbance range of about 0.009 AU to about 0.017 AU;
a second fraction having an absorbance range of about 0.005 AU to about 0.010 AU;
a third fraction having an absorbance range of about 0.010 AU to about 0.018 AU;
a fourth fraction having an absorbance range of about 0.018 to about 0.030 AU;
a fifth fraction having an absorbance range of about 0.030 AU to about 0.090 AU;
a sixth fraction having an absorbance range of about 0.030 AU to about 0.080 AU; and
a seventh fraction having an absorbance range of about 0.025 AU to about 0.030 AU.

* * * * *